United States Patent [19]

McLaughlin

[11] Patent Number: 5,003,068
[45] Date of Patent: Mar. 26, 1991

[54] PYRIDAZINONE MANUFACTURE
[75] Inventor: Thomas A. McLaughlin, Penndel, Pa.
[73] Assignee: Monsanto Company, St. Louis, Mo.
[21] Appl. No.: 406,650
[22] Filed: Sep. 13, 1989
[30] Foreign Application Priority Data
Sep. 13, 1988 [GB] United Kingdom ................. 8821447
[51] Int. Cl.$^5$ .......................................... C07D 237/14
[52] U.S. Cl. ................................... 544/239
[58] Field of Search ....................... 544/239; 514/247
[56] References Cited
U.S. PATENT DOCUMENTS
2,783,232 2/1957 Gutmann ............................ 544/239
4,561,881 12/1985 Labovitz ............................. 544/239
4,623,378 11/1986 Dürrr ................................. 544/239

OTHER PUBLICATIONS

Plescia, S. et al. Jour. Het. Chem. vol. 18, pp. 333-334 (1981).

Primary Examiner—Donald G. Daus
Attorney, Agent, or Firm—Howard C. Stanley; Grace L. Bonner

[57] ABSTRACT

An improved method for the manufacture of a substituted 1,4-dihydro-4-oxopyridazine which comprises the step of reacting a glyoxyclic acid halide phenylhydrazone with 3-pyrrolidinyl-2-alkenoic acid ester.

5 Claims, No Drawings

PYRIDAZINONE MANUFACTURE

This invention relates to the manufacture of carboxylate substituted 1,4-dihydro-4-oxopyridazines useful as intermediates for 4-pyridazinone carboxylic acids of formula (I):

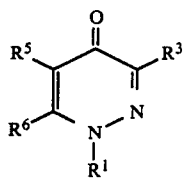

where: $R^1$ is a phenyl group, optionally substituted with, e.g., alkyl or halo groups, $R^3$ is H, alkyl, halo or carboxy group, at least one of $R^3$ and $R^5$ being carboxy; $R^5$ is H or a carboxy group; $R^6$ is H or alkyl.

Compounds of formula (I) are useful as plant growth regulating compounds, and in particular as chemical hybridizing agents. They have found use as male sterilants for cereal crops, for example wheat and barley, and are useful for making hybrids in such crops.

It is known from European Patent Application No. 49971 to manufacture compounds of the above formula according to the following reaction scheme.

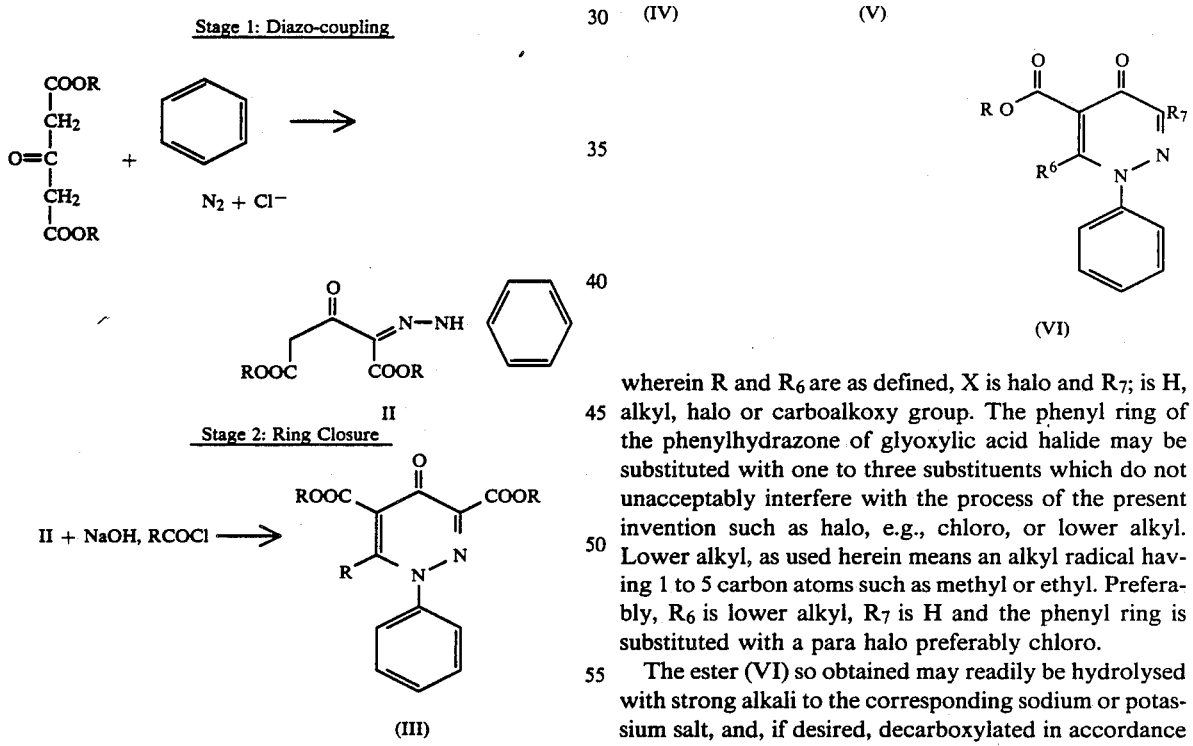

where R is alkyl, the compound (III) so obtained may then be hydrolyzed either partially to the mono ester or completely to the dicarboxylic acid; and if desired the resulting dicarboxylic acid may be partially de-carboxylated generally in accordance with procedures set forth in U.S. Pat. No. 4,732,603; 4,661,145 and 4,707,181 which are incorporated herein by reference. This generally gives a mixture of the two possible monocarboxylic acids, from which the desired product may be recovered by art known procedures.

A problem with the above process is a possibility for polychlorinated biphenyls (PCBs) to be produced in Stage 1 (diazo-coupling). Since PCBs are toxic and persist in the environment, considerable care and expense must be undertaken to recover any PCBs produced from the reaction mixture and dispose of them safely.

The present invention provides a novel method of producing 4-pyridazinone carboxylic acids which uses a novel cyclization step, and avoids Stage 1 of prior process.

The present invention provides a process for the production of substituted 1,4-dihydro-4-oxopyridazine comprising reacting a phenylhydrazone of glyoxylic acid halide with a 3-pyrrolidinyl-2-alkenoic acid ester generally, according to the following scheme:

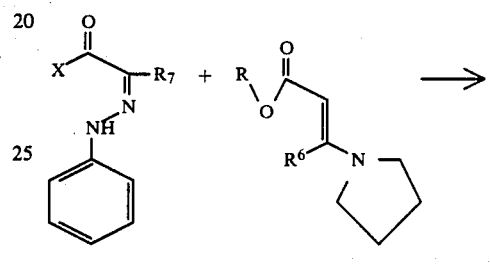

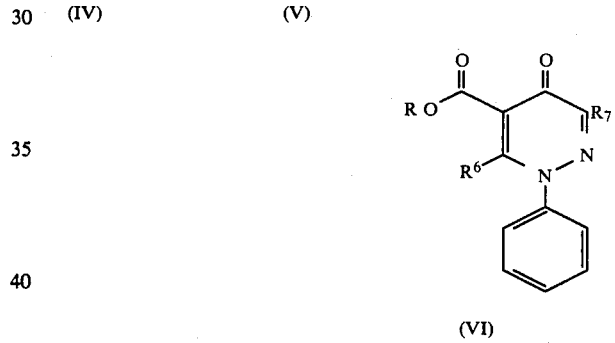

wherein R and $R_6$ are as defined, X is halo and $R_7$; is H, alkyl, halo or carboalkoxy group. The phenyl ring of the phenylhydrazone of glyoxylic acid halide may be substituted with one to three substituents which do not unacceptably interfere with the process of the present invention such as halo, e.g., chloro, or lower alkyl. Lower alkyl, as used herein means an alkyl radical having 1 to 5 carbon atoms such as methyl or ethyl. Preferably, $R_6$ is lower alkyl, $R_7$ is H and the phenyl ring is substituted with a para halo preferably chloro.

The ester (VI) so obtained may readily be hydrolysed with strong alkali to the corresponding sodium or potassium salt, and, if desired, decarboxylated in accordance with the above-described procedures to form a plant growth regulatory or chemical hybridizing agent.

The compound (V) in the above scheme R is alkyl preferably lower alkyl, e.g., methyl or ethyl, and $R^6$ is H or alkyl, preferably lower alkyl such as methyl, ethyl, propyl or isopropyl. Compound (V) is readily obtained by reaction of pyrrolidine with an appropriate 3-oxoalkanoic acid ester.

The compound (IV) can be prepared generally in accordance with the following procedure:

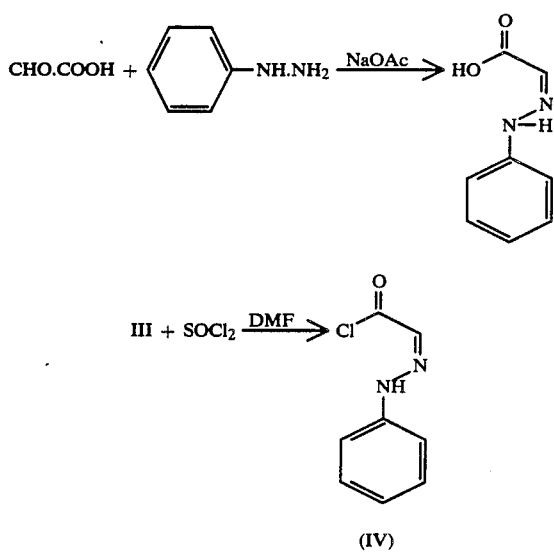

The process of the invention may be carried out at moderate temperatures and normal pressures. It is preferred to carry out the reaction at between 0° and 25° C. It is convenient to carry out the reaction in an inert organic solvent, e.g., methylene dichloride.

The process of the invention is useful for making intermediates for compounds of formula (I), and the starting materials are readily available and inexpensive. Yields in excess of 80% are obtainable.

The following Example illustrates the invention.

EXAMPLE 1

Preparation of 1-p-chlorophenyl-1,4-dihydro-4-oxo-6-ethyl-5-carboxylic acid.

A. Preparation of Methyl Ester of 3-Pyrrolidinyl-2-Pentenoic Acid

A mixture of pyrrolidine (192g), methyl propionyl acetate (87.8 g), and benzene (500 ml) in a 1-litre round-bottomed flask equipped with magnetic stirrer, Dean-Start trap and reflux condenser was heated at reflux until all of the water was removed in the azeotrope (about 4-5 hours).

Excess pyrrolidine and benzene were distilled off a 60° C. and 20 mm pressure. The residue of methyl-3-pyrrolidinyl-2-pentenoate was 99% pure by G.C. analysis and weighed 125.7 g.

Further purification was accomplished by distillation at 1.7 mm pressure when the material was found to boil at 125°-131° C. and to be 100% pure by G.C. analysis.

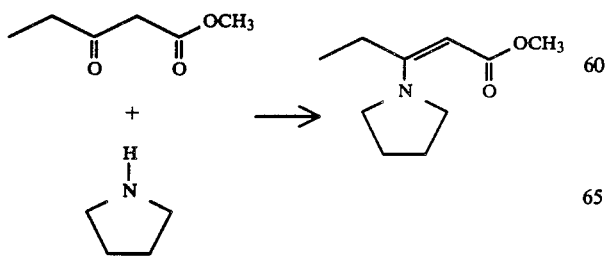

B. Preparation of p-Chlorophenyl Hydrazone of Glyoxylic Acid (III)

Purified p-chlorophenyl hydrazine hydrochloride (1 equivalent) dissolved in a convenient volume of de-ionised water was added dropwise to a solution of glyoxylic acid (1 equivalent) and sodium acetate (1.5 equivalent) in a convenient volume of de-ionised water with adequate agitation and ice cooling. The resulting precipitate was vacuum filtered and washed with water. The solid was dried thoroughly in vacuum at 60° C. Yield of yellow solid was near quantitative, mp 145° C. with decomposition.

C. Preparation of p-Chlorophenyl Hydrazone of Glyoxylic Acid Chloride (IV)

The dried p-chlorophenyl hydrazone of glyoxylic acid (III) was slurried in a flame dried 200 ml round-bottomed flask in 50 ml of dry methylene dichloride (over 4A (molecular sieves), and five drops of dry DMF then added. Thionyl chloride (10% excess of 1 equivalent) was added and the mixture warmed to a gentle reflux until evolution of acidic vapours was complete and a dark coloured solution formed (time required was 40 minutes). The solution was degassed under 20-25 mm reduced pressure whereupon copious yellow crystals separated from the now cool reaction mixture.

D. Preparation of Methyl 1-(4-chlorophenyl)-1,4-dihydro-6-ethyl-4-oxo-pyridazine-5-carboxylate (VI)

Methyl 3-pyrrolidino-2-pentenoate (V) (1 equivalent: this may be prepared as in A above) was dissolved in a 500 ml round-bottomed flame dried flask in 50 ml of dry methylene dichloride. The solution was stirred magnetically and cooled in an ice bath as the acid chloride was added dropwise from a pressure equalizing addition funnel. Additional methylene dichloride as required was used to rinse in the crystalline portion of the acid chloride. The wine-coloured reaction solution was stirred for an additional 30 minutes with ice cooling and then overnight at room temperature. Finally, a gentle reflux period of two hours was employed to ensure complete reaction. TLC showed the desired product had been obtained.

E. Product Isolation

The reaction solution was cooled and washed with a 100 ml portion of water, two 100 ml portions of 5aqueous NaOH, and again with a 100 ml portion of water. After drying over anhydrous sodium sulphate, the methylene dichloride was distilled off leaving a brown solid residue.

F. Purification

Three options are available for purification of the product:

(1) Trituration at the ester (VI) state with anhydrous diethyl ether renders (VI) as an insoluble near white crystalline solid with purity—98% (TLC). Some product remains in the ether portion, the amount depending upon the volume of ether employed.

(2) Wet column chromatography using a solvent gradient system hexane to ethyl acetate on silica gel gives quantitative recovery of 100% pure ester (VI).

(3) Saponification of the crude ester (VI) using excess aqueous NaOH, methylene chloride extraction of the aqueous alkaline solution, and precipitation with mineral acid produces the free acid pyridazinone in quantitative yield with 98% purity (TLC).

What is claimed is:

1. Process for the production of a substituted 1,4-dihydro-4-oxopyridazine which comprises reacting a phenylhydrazone of glyoxylic acid halide with a 3-pyrrolidinyl-2-alkenoic acid ester.

2. Process as claimed in claim 1 which is conducted in the presence of an inert organic solvent.

3. Process as claimed in claim 2 which is conducted at a temperature between 1° to 25° C.

4. Process as claimed in any of claims 1 to 3 in which the phenyl group of the phenylhydrazone is substituted with halogen or lower alkyl groups.

5. Process for the production of methyl 1-(4-chlorophenyl)-1,4-dihydro-6-ethyl-4-oxo-pyridazine-5-carboxylate which comprises reacting p-chlorophenyl hydrazone of glyoxylic acid chloride with methyl 3-pyrrolidino-2-pentenoate.

* * * * *